United States Patent [19]

van Zelderen

[11] Patent Number: Plant 5,712

[45] Date of Patent: Apr. 8, 1986

[54] ALSTROEMERIA NAMED ZELANON

[75] Inventor: Gerard J. van Zelderen, Aalsmeer, Netherlands

[73] Assignee: J. van Zelderen & Zn., Aalsmeer, Netherlands

[21] Appl. No.: 652,602

[22] Filed: Sep. 19, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new alstroemeria variety characterized by the distinctive coloration of its large blossoms with numerous longitudinal flecks or streaks of purple in the marginal areas of the outer petals and throughout the entire areas of the inner petals. The inner petals are of a white background color and the outer petals have background colors of white in their marginal areas and light purple in their central areas. The plant is also characterized by its upright and vigorous growth habit and the continuous production of flowers on its umbel arrangement of branches during each of its blooming seasons.

1 Drawing Figure

BACKGROUND OF THE NEW PLANT

This new alstroemeria originated as a seedling and resulted from my crossing of plants (unpatented) selected from individually-identified members of stock maintained at Aalsmeer, Holland for breeding purposes. This particular seedling was selected by me for propagating and testing because of the distinctive coloration of its large blossoms produced on strong, upright, umbel stems. Specifically, the outer petals have purple central areas and white marginal areas, the inner petals have a white background color, and both the outer and inner petals have well-defined longitudinal streaks of deeper purple, such streaks of the outer petals being generally limited to their lateral marginal areas. The selected plant was propagated by me at Aalsmeer, Holland through several generations by root division to establish that its distinctive characteristics hold true from generation to generation and appear to be firmly fixed. Breeding efforts commenced in 1979 and propagation is currently being carried out at Aalsmeer, Holland by dividing root stocks.

DESCRIPTION OF THE DRAWING

This new variety of alstroemeria plant is illustrated by the accompanying photographic drawing in full color showing a blooming umbel of the plant with buds and flowers in different stages of opening. The color renditions are believed to be as close to the specified colors as is possible to obtain by conventional photographic procedures.

DESCRIPTION OF THE NEW PLANT

The following is a detailed description of my new alstroemeria plant with color designations according to The R.H.S. Colour Chart of The Royal Horticultural Society of London, England. Cross references to the color names appearing in The Horticultural Colour Chart (H.C.C.) of London, England, are also parenthetically indicated.

THE PLANT

Origin: Seedling.

Parentage:

*Seed parent.*—Breeding Stock Plant No. 790204.

*Pollen parent.*—Breeding Stock Plant No. 760605.

Classification: Alstroemeria Hybrid.

Form: An erect bush having a tall, slender, upright stalk with flower-bearing branches in simple umbel arrangement at its top.

Height: About 140 centimeters.

Growth: Upright, strong, and vigorous.

Root stock: Tuberous.

Foliage:

*Quantity.*—Medium.

*Number of leaves.*—About 20 per stem, depending on season.

*Size of leaf.*—Varies depending on season.

*Shape of leaf.*—Elliptic.

*Texture.*—Leathery.

*Color.*—Upper sides: medium green Underside: medium gray-green.

THE BUD

Form: Pear-shaped. The six petals are perianth and there is no calyx.

Size: Large.

*Diameter.*—About 2 centimeters.

*Length.*—About 4.5 centimeters.

Length of peduncle: About 4 centimeters.

THE FLOWER

Blooming habit: Continuous during midseason in Spring and Fall.

Flower size: Large.

*Diameter.*—About 5.5 centimeters.

*Depth.*—About 7 centimeters.

Borne: Singly.

Shape: Generally funnel-like with petal tips curling outwardly.

Petalage:

*Number of petals.*—Six.

*Arrangement.*—Two concentric circles of three.

*Form.*—Broad oval.

*Texture.*—Leathery.

*Appearance.*—Shiny.

Color:

*Outer petals.*—General background color is white 155C with lateral marginal areas having sharplydefined greyed-purple streaks 185A and with shading in their central areas of lighter purple 77C. The reverse sides of the outer petals are purple 77D.

*Inside petals.*—A white base color of 155C with numerous well-defined longitudinal greyed-purple streaks of 185A throughout. The reverse sides of the outer petals are purple 77C.

Persistence: The flowers hang and dry. The blooms appear uneffected by wet or hot weather and there is no or little discoloration after full bloom.

Main stem or stalk:

*Length.*—About 140 centimeters.

*Color.*—Medium green.

*Character.*—Strong and upright.

*Lasting quality of flower.*—On the plant — 15 to 20 days. As a cut flower — 10 to 15 days.

REPRODUCTIVE ORGANS

Stamens:

*Number.*—Six.

*Arrangement.*—One opposite each petal.

*Anthers.*—Size: About one centimeter. Color: Gray.

Filaments:

*Length.*—About 4 centimeters.

*Color.*—Violet/pink.

*Pollen.*—Gray.

Pistils:

*Number.*—One.

*Styles.*—Length: About 0.8 to 1 centimeter. Color: Violet/pink.

*Fruit.*—Shape: Capsular. Color: Light brown at maturity.

This plant is particularly noted for the distinctive coloration of its flowers, which coloration does not closely resemble that of any other alstroemeria plant previously known to me. The large blossoms of this varietal have outer petals of a white background with longitudinal streaks or flecks of deep greyed-purple in the lateral marginal areas and with central areas of a lighter purple background, and the inner petals have a white background with numerous deep greyed-purple streaks throughout. The cultivar has a vigorous growth habit and, during its Spring and Fall blooming seasons, a continuous production of flowers that resist adverse effects of wet or hot weather and notably retain their coloration after full bloom.

I claim:

1. A new and distinctive alstroemeria cultivar, substantially as shown and described, characterized by the distinctive coloration and continuous production of its large blossoms with their white outer petals having marginal areas with numerous longitudinal streaks of purple and central areas shaded in lighter purple, and with their white inner petals having numerous longitudinal streaks of purple throughout.

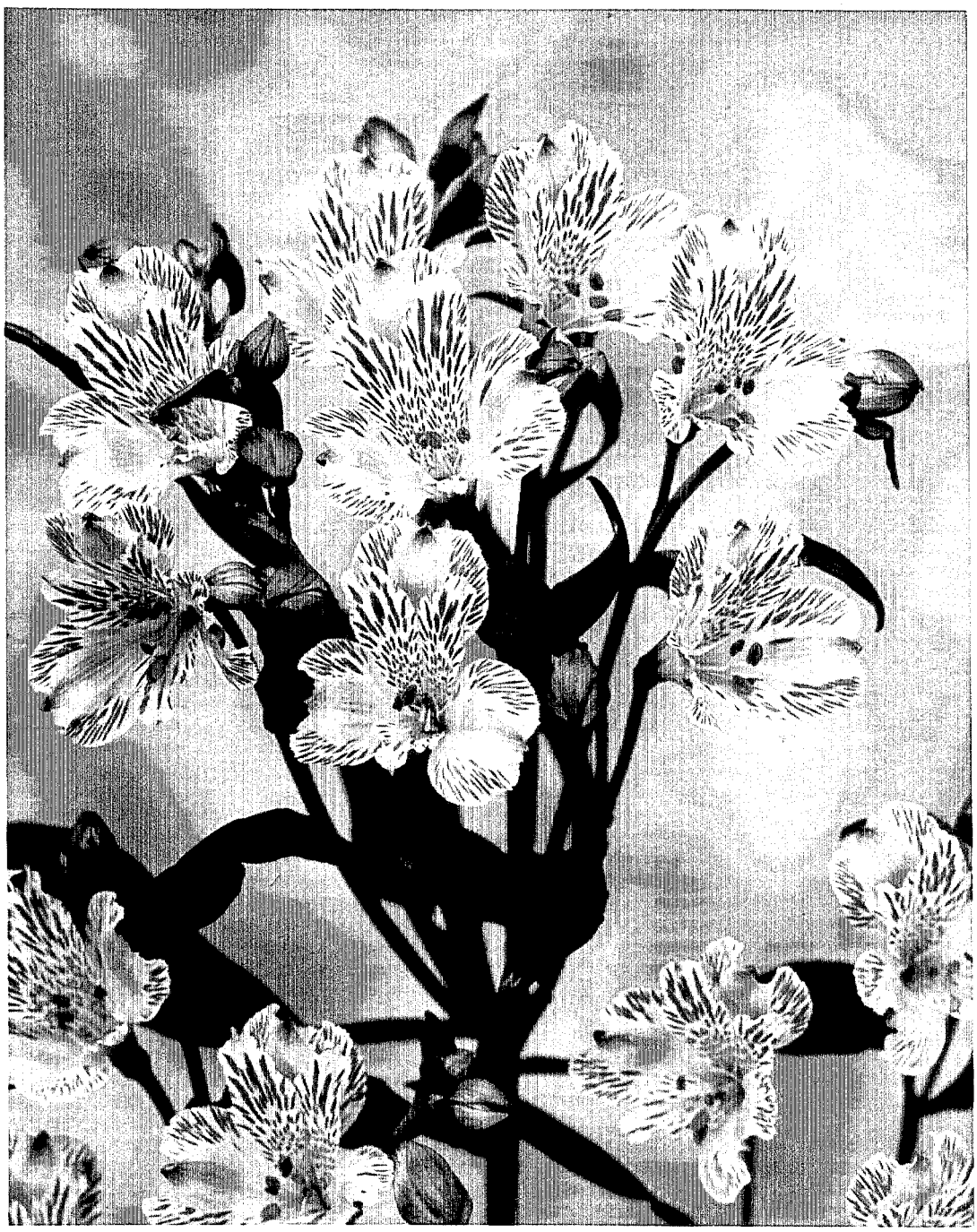

* * * * *